US010400205B2

(12) United States Patent
Köll et al.

(10) Patent No.: US 10,400,205 B2
(45) Date of Patent: Sep. 3, 2019

(54) STIRRING DEVICE

(71) Applicant: THÖNI INDUSTRIEBETRIEBE GMBH, Telfs (AT)

(72) Inventors: Thomas Köll, Telfs (AT); Daniel Kern, Kloten (CH); Michael Krismer, Landeck (AT)

(73) Assignee: THÖNI INDUSTRIEBETRIEBE GMBH, Telfs (AT)

( * ) Notice: Subject to any disclaimer, the term of this patent is extended or adjusted under 35 U.S.C. 154(b) by 408 days.

(21) Appl. No.: 14/911,544

(22) PCT Filed: Aug. 12, 2014

(86) PCT No.: PCT/EP2014/067202
§ 371 (c)(1),
(2) Date: Feb. 11, 2016

(87) PCT Pub. No.: WO2015/022305
PCT Pub. Date: Feb. 19, 2015

(65) Prior Publication Data
US 2016/0186117 A1 Jun. 30, 2016

(30) Foreign Application Priority Data

Aug. 16, 2013 (EP) ..................................... 13180752

(51) Int. Cl.
B01F 7/16 (2006.01)
C12M 1/06 (2006.01)
(Continued)

(52) U.S. Cl.
CPC ......... C12M 27/02 (2013.01); B01F 7/00158 (2013.01); B01F 7/028 (2013.01);
(Continued)

(58) Field of Classification Search
CPC ......................................................... B01F 7/16
(Continued)

(56) References Cited

U.S. PATENT DOCUMENTS 5,560 A * 5/1848 Chapin ............... B01F 7/00158
366/325.1
RE137 E * 5/1849 Chapin ...................... 366/325.1
(Continued)

FOREIGN PATENT DOCUMENTS

CN 202087251 U 12/2011
CN 202666729 U 1/2013
(Continued)

OTHER PUBLICATIONS

Chinese Office action issued in parallel Chinese Application No. 201480045297 dated Mar. 3, 2017, 7 pages.

Primary Examiner — David L Sorkin
(74) Attorney, Agent, or Firm — Lewis Roca Rothgerber Christie LLP

(57) ABSTRACT

In accordance with embodiments of the herein disclosed subject matter it is described a stirring device (100) comprising a shaft rotatable about an axis of rotation; a stirring element (106) attached to the shaft, the stirring element (106) having a recess (108); the recess (108) having a surface portion (114) and an edge (116), the edge (116) defining an opening which provides access to the surface portion (114); the recess (108) being spaced from the shaft, wherein a rotation of the shaft defines a moving direction (120) of the recess (108) in which the edge (116) forms a leading edge of the recess (108); the surface portion (114) defining a depth (122) of the recess (108) with regard to the edge (116); and wherein in a direction (124) radially inwardly the depth (122) of the recess (108) is decreasing. In accordance with embodiments, the decreasing depth (122) may be realized by a suitable inclination (136) of the
(Continued)

surface portion (114) of the recess (116) and/or by a suitable inclination (140) of the edge (116) of the recess (108).

14 Claims, 2 Drawing Sheets

(51) Int. Cl.
*B01F 7/00* (2006.01)
*B01F 7/02* (2006.01)
*B01F 7/04* (2006.01)
*C12M 1/107* (2006.01)

(52) U.S. Cl.
CPC ................ *B01F 7/04* (2013.01); *B01F 7/16* (2013.01); *C12M 21/04* (2013.01); *B01F 2215/0073* (2013.01); *Y02E 50/343* (2013.01)

(58) Field of Classification Search
USPC ...................................................... 366/325.1
See application file for complete search history.

(56) References Cited

U.S. PATENT DOCUMENTS

| | | | | |
|---|---|---|---|---|
| 836,565 | A | * 11/1906 | Daum | ..................... F28F 13/12 |
| | | | | 165/109.1 |
| 1,011,317 | A | * 12/1911 | Carlton et al. | .......... C02F 1/686 |
| | | | | 137/98 |
| 2,433,478 | A | 12/1947 | Nelson | |
| 3,079,241 | A | 2/1963 | Glazenburg | |
| 5,981,269 | A | * 11/1999 | Park | .................... C05F 17/0018 |
| | | | | 366/325.1 |

FOREIGN PATENT DOCUMENTS

| | | |
|---|---|---|
| DE | 201 16 967 U1 | 2/2002 |
| EP | 2 561 925 A1 | 2/2013 |
| GB | 276266 | 8/1927 |
| SU | 1692631 A1 | 11/1991 |
| WO | WO 03/033124 A1 | 4/2003 |

* cited by examiner

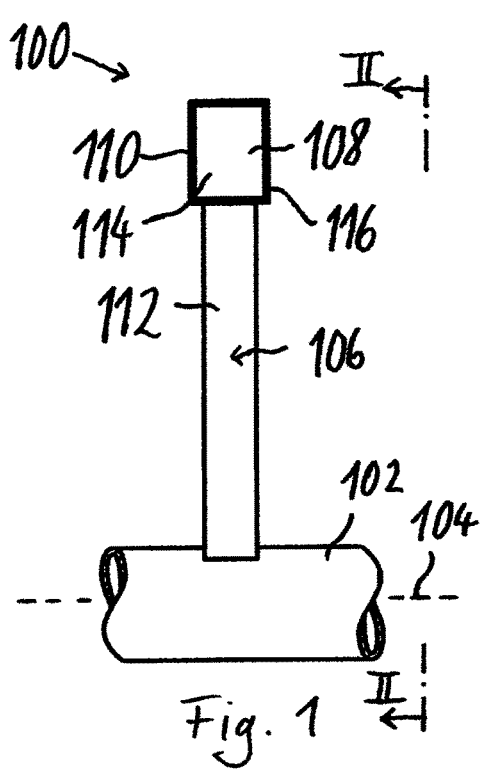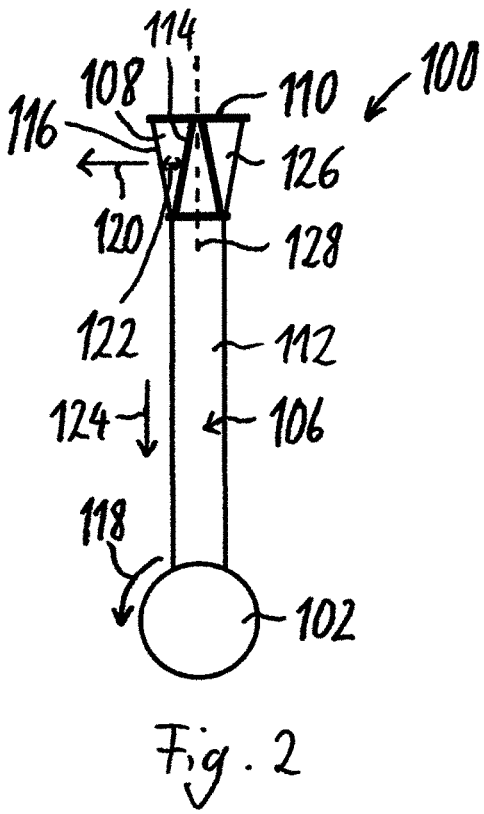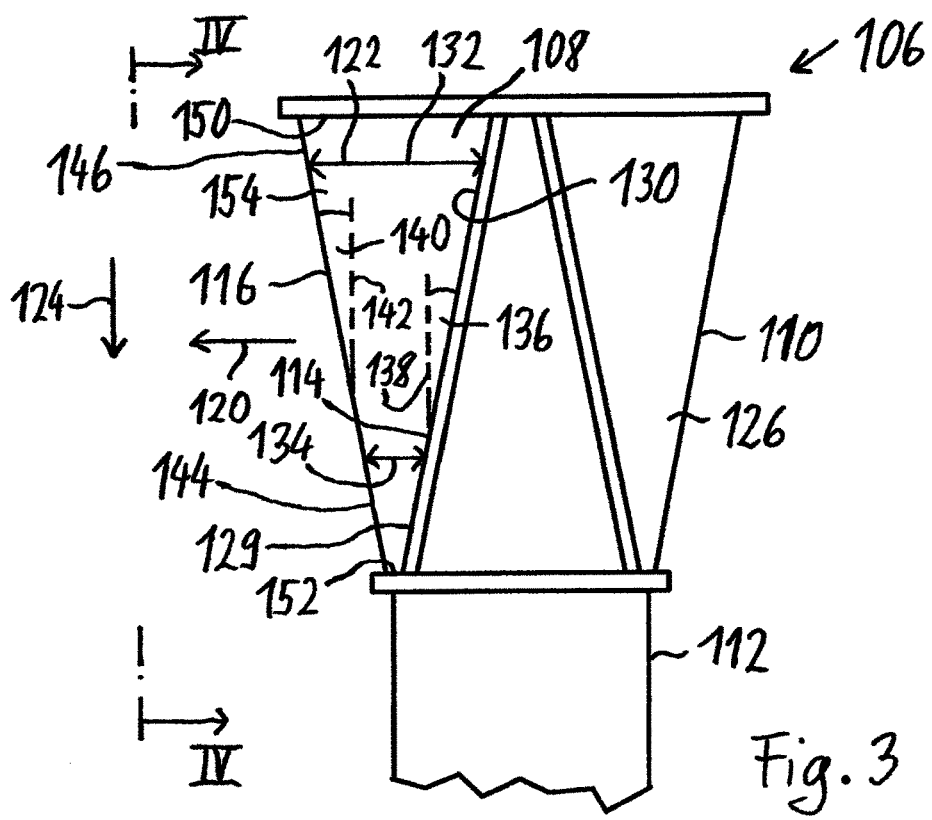

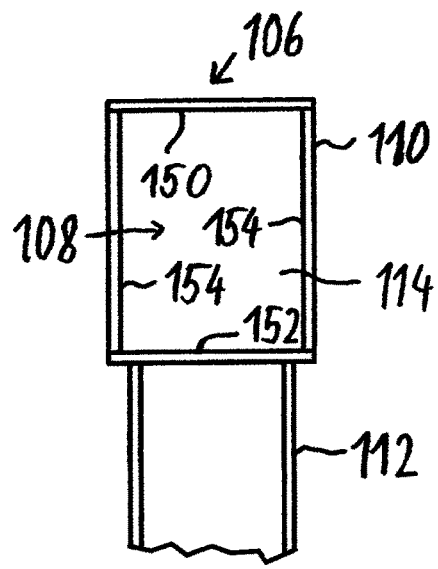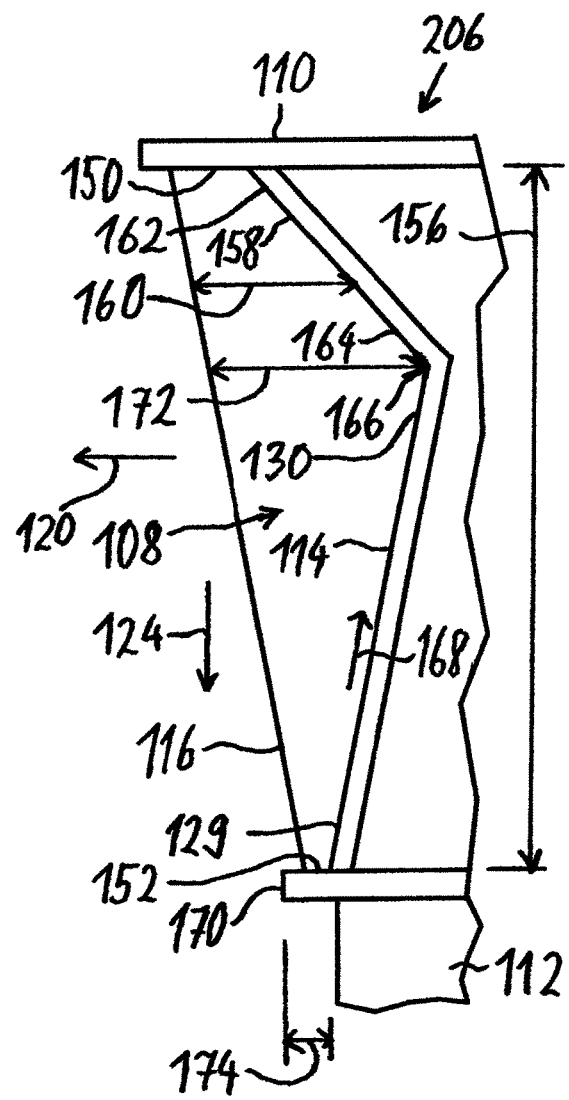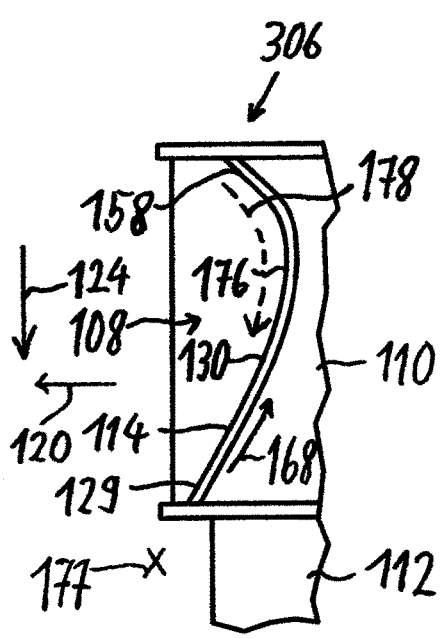

STIRRING DEVICE

CROSS-REFERENCED TO RELATED APPLICATION(S)

This Application is a National Phase Patent Application and claims priority to and the benefit of International Application Number PCT/EP2014/067202, filed on Aug. 12, 2014, which claims priority to and the benefit of European Patent Application No. 13180752.1, filed Aug. 16, 2013, the entire contents of all of which are incorporated herein by reference.

FIELD OF INVENTION

The present invention relates to the field of stirring devices for a biogas fermenter.

BACKGROUND

EP 2 561 925 A1 discloses a stirring element with a head comprising two recesses pointing in opposite directions, wherein each recess points in a circumferential direction.

SUMMARY

In view of the above-described situation, there exists a need for an improved technique that enables to provide a stirring device for a biogas fermenter which provides for an efficient stirring of fermentation material in the biogas fermenter.

This need may be met by the subject matter according to the independent claims. Advantageous embodiments of the herein disclosed subject matter are described by the dependent claims.

According to an embodiment of a first aspect of the herein disclosed subject matter there is provided stirring device for a biogas fermenter, the stirring device being configured for stirring a fermentation material, the stirring device comprising: a shaft rotatable about an axis of rotation; a stirring element attached to the shaft, the stirring element having a recess; the recess having a surface portion and an edge, the edge defining an opening which provides access to the surface portion; the recess being spaced from the shaft, wherein a rotation of the shaft defines a moving direction of the recess in which the edge forms a leading edge of the recess; the surface portion defining a depth of the recess with regard to the edge; wherein in a direction radially inwardly the depth of the recess is decreasing.

During an upward movement of the stirring element, in the course of the rotation of the stirring element about the axis of rotation, some fermentation material (e.g. sediment) is contained in the recess and is moved by the recess through the fermentation material contained in the fermenter. During its subsequent downward movement, with the opening of the recess pointing downwards, most of the fermentation material in the recess falls out of the recess, making the recess available for pickup of further fermentation material. However, in the conventional stirring elements, e.g. as described in EP 2 561 925 A1 in particular sediment may stick to the recess, thereby reducing the effective volume of the recess.

The first aspect of the herein disclosed subject matter is based on the idea that the inwardly decreasing depth of the recess with regard to its opening edge facilitates removal of fermentation material contained in the recess since a resistance against radially inward emptying of the recess is reduced. On the other hand embodiments of the herein disclosed subject matter take into account that during stirring of a fermentation material in a biogas fermenter, and in particular in a plug flow fermenter, high forces are acting on the individual stirring elements.

Although herein reference is usually made to a single stirring element, it should be understood that the stirring device usually includes a plurality of stirring elements.

Generally herein, the terms "direction radially inwardly", "radially inward direction", "radially", "radio", "radially inner", "radially outer", etc. refer to the stirring element under discussion and are defined with respect to the stirring element.

The stirring device according to embodiments of the herein disclosed subject matter is in particular suitable for plug flow fermenters and fermenters for dry fermentation wherein the fermentation material has a dry substance content of 15% or more, e.g. of 20% or more, e.g. of 25% or more or 30% or more.

Generally herein, the term "axial direction" refers to a direction parallel to the shaft and/or parallel to its axis of rotation, unless otherwise noted.

According to an embodiment, the surface portion has a radially inner part and a radially outer part, wherein the radially inner part is located between the axis of rotation and the radially outer part and wherein the surface portion is configured such that in a movement of the recess in the moving direction the radially inner part is a leading part and the radially outer part is trailing the radially inner part. For example, according to an embodiment the surface portion is inclined with regard to a plane which is perpendicular to the moving direction. Hence, with regard to an non-inclined surface portion (which is perpendicular to the moving direction) the inclined surface portion moves the fermentation material contained in the recess more to the edge of the recess under the action of gravity if the stirring element is pointing upward, e.g. if the stirring element is between its 10 o'clock and its 2 o'clock position.

According to an embodiment, the edge has a radially inner edge portion and a radially outer edge portion, wherein the radially inner edge portion is located between the axis of rotation and the radially outer edge portion; the edge being configured such that in a movement of the recess in the moving direction the radially outer edge portion is a leading portion and the radially inner edge portion is trailing the radially outer edge portion. For example, according to an embodiment the edge of the recess is inclined with regard to a plane which is perpendicular to the moving direction. Hence, with regard to a non-inclined edge of the recess the inclined edge has its radially inner edge portion located closer to the surface portion.

According to an embodiment, the recess has a straight or continuously curved edge.

According to a further embodiment, the surface portion forms at least part of a bottom of the recess. Generally, the bottom of the recess may be defined as a portion of the recess which defines a depth of the recess.

The recess may be laterally defined by at least one wall. For example, in an embodiment where the opening of the recess has a tetragonal shape, the recess optionally comprises four walls which extend from the edge of the recess to the bottom of the recess. According to an embodiment, the walls extend in the moving direction. A tetragonal shape as the advantage of providing a large area transverse to the moving direction while being relatively easy to manufacture.

According to an embodiment, the recess comprises a further surface portion, wherein the surface portion is located between the further surface portion and the axis of rotation; the further surface portion defining a depth of the recess with regard to the edge. In other words, in this embodiment the recess comprises at least two surface portions, the aforementioned surface portion and the further surface portion. According to an embodiment, also the further surface portion forms part of the bottom of the recess. According to an embodiment, the further surface portion is configured for improving emptying of the recess during movement of the recess outside the fermentation material in the fermenter, between emerging from and again submerging into the fermentation material, for instance between the 10 o'clock position and the 2 o'clock position of the stirring element, e.g. in a 12 o'clock position of the stirring element, where the stirring element extends vertically upward.

According to an embodiment, at least one of the surface portion and the further surface portion is flat surface portion. According to a further embodiment, at least one of the surface portion and the further surface portion is a curved surface portion.

According to an embodiment, the further surface portion has a first part and a second part, wherein the second part of the further surface portion is located between the first part of the further surface portion and the radially outer part of the surface portion; the further surface portion being configured such that in a movement of the recess in the moving direction its first part is a leading part and its second part is trailing the first part. For example, according to an embodiment the further surface portion is inclined with regard to a plane which is perpendicular to the moving direction, wherein the surface portion and the further surface portion are inclined towards each other, forming an angle less than 180 degrees between the surface portion and the further surface portion.

According to an embodiment, the stirring element comprises an intermediate surface portion located between the surface portion and the further surface portion, the intermediate surface portion connecting the surface portion and the further surface portion to a continuous surface of the recess. According to an embodiment, the intermediate surface portion is curved surface portion. For example, according to an embodiment the intermediate surface portion has slope which continuously changes from the slope of the further surface portion to the slope of the surface portion, thereby forming a curvature.

According to a further embodiment, the surface portion and the further surface portion abut in a kink. In combination with the embodiment where the surface portion and the further surface portion are flat surface portions, this embodiment allows for a cost efficient manufacture of the stirring element. In particular, according to an embodiment the stirring element is formed from pieces of a flat plate elements while still providing advantages as disclosed herein. For example, the walls and the bottom may be formed of flat plate elements which are attached (e.g. welded) together.

According to an embodiment, the surface portion extends in radial direction over at least a 10% of the radial extent of the recess. According to other embodiments, the surface portion extends in the radial direction over at least 15%, 20%, 30%, 40%, 50%, 60%, 70%, 80%, or 100%, respectively. The larger the radial extent of the surface portion is, the larger is the effect of the decreasing depth in the radially inward direction. According to other embodiments, the surface portion extends in the radial direction over 15%, 20%, 30%, 40%, 50%, 60%, 70%, 80%, or 100%, respectively, or less. It should be understood that the disclosure of the above percentages for the minimum extent and the maximum extent of the surface portion include, in the combination of a minimum extent and a maximum extent which is larger than the minimum extent, respective extension ranges in which the extent for the surface portion falls in respective embodiments.

According to a further embodiment, the surface portion extends straight in a first direction. For example, in an embodiment, the surface portion is a flat surface portion, as mentioned above. In other embodiments, the surface portion is curved while optionally still extending straight in the first direction. For example, according to an embodiment the first direction is parallel to the axis of rotation. In other words, according to an embodiment, the first direction is the axial direction. In this embodiment the surface portion may be formed by a piece of sheet metal which is attached to sidewalls of the recess, thereby forming a bottom portion of the recess. According to an embodiment, the first direction forms an angle with the axial direction, thereby generating material transport in axial direction upon movement of the recess in the moving direction.

According to an embodiment, the surface portion is curved, e.g. continuously bent, in a direction from its radially inner part to its radially outer part. This may generate a flow of fermentation material in the recess in radial direction upon moving the recess through the fermentation material in the moving direction. The flow of fermentation material in the recess reduces or eliminates an accumulation of sediment in the recess. According to an embodiment, the surface portion is configured for generating a flow of fermentation material in the recess. For example according to an embodiment this is achieved by the surface portion being curved in a direction perpendicular to the axial direction and optionally by the first direction being the axial direction or has at least having a non-zero component in the axial direction. The further surface portion may be configured in a similar way, i.e. extending straight in the first direction wherein the first direction is the axial direction or has at least a non-zero component in the axial direction while the further surface portion is curved in a direction perpendicular to the axial direction. According to an embodiment, the whole bottom of the recess is formed in this way.

According to a further embodiment, the surface portion extends straight in a direction from its radially inner part to its radially outer part. In this embodiment, the surface portion may be curved in axial direction or may extend straight in axial direction.

According to an embodiment, the edge of the recess comprises an radially innermost edge portion, wherein the radially inner part of surface portion is located in the vicinity of the radially innermost edge portion of the edge. According to an embodiment, the vicinity of any point on the radially innermost edge portion is defined by a distance to this point which is less than 50% of the maximum depth of the recess in the moving direction. According to further embodiments, the vicinity of any point on the radially innermost edge portion is defined by a distance to this point which is less than 40%, 30%, 20%, 10%, or 5% of the maximum depth of the recess in the moving direction, respectively. Having the radially inner part of the surface portion located in the vicinity of the radially innermost edge portion of the edge of the recess may have the advantage of a low resistance for the fermentation material contained in the recess to empty out of the recess in radially inward direction.

According to an embodiment, the at least one wall of the recess comprises a radially inner wall which extends in the moving direction; the radially inner wall of the recess forming the radially innermost edge portion of the edge of the recess; and the surface portion abutting the radially inner wall spaced from the radially inner edge portion. This feature may improve the flow of fermentation material within the recess.

In the above there have been described and in the following there will be described exemplary embodiments of the subject matter disclosed herein with reference to a stirring device for a biogas fermenter. It has to be pointed out that of course any combination of features relating to different aspects of the herein disclosed subject matter is also possible. In particular, some features have been or will be described with reference to apparatus type embodiments whereas other features have been or will be described with reference to method type embodiments. However, a person skilled in the art will gather from the above and the following description that, unless other notified, in addition to any combination of features belonging to one aspect also any combination of features relating to different aspects or embodiments, for example even combinations of features of apparatus type embodiments and features of the method type embodiments are considered to be disclosed with this application.

The aspects and embodiments defined above and further aspects and embodiments of the herein disclosed subject matter are apparent from the examples to be described hereinafter and are explained with reference to the drawings, but to which the invention is not limited. Statements and explanations given above are also valid for the description of the examples given below and vice versa.

BRIEF DESCRIPTION OF THE DRAWINGS

FIG. 1 shows part of a stirring device for a biogas fermenter according to embodiments of the herein disclosed subject matter.

FIG. 2 shows a side view of the stirring element shown in FIG. 1 when viewed from line II-II in FIG. 1.

FIG. 3 shows the stirring element of FIG. 1 in greater detail.

FIG. 4 shows the stirring element of FIG. 3 when viewed from line IV-IV in FIG. 3.

FIG. 5 shows in cross-sectional view a part of a further stirring element in accordance with embodiments of the herein disclosed subject matter.

FIG. 6 shows in cross-sectional view a part of a further stirring element in accordance with embodiments of the herein disclosed subject matter.

DETAILED DESCRIPTION

The illustration in the drawings is schematic. It is noted that in different figures, similar or identical elements are provided with the same reference signs or with reference signs which are different from the corresponding reference signs only within the first digit. Accordingly, the description of similar or identical features is not repeated in the description of subsequent figures in order to avoid unnecessary repetitions. However, it should be understood that the description of these features in the preceding figures is also valid for the subsequent figures unless noted otherwise.

FIG. 1 shows part of a stirring device 100 for a biogas fermenter according to embodiments of the herein disclosed subject matter.

The stirring device comprises a shaft 102 which is rotatable about an axis of rotation 104. According to an embodiment, the shaft 102 is hollow shaft, as shown in FIG. 1. Attached to the shaft 102 are a plurality of stirring elements 106, one of which is shown in FIG. 1. The stirring element 106 comprises a recess 108. According to an embodiment, the recess 108 is formed by a head 110 of the stirring element 106. According to an embodiment, the head 110 is mounted to the shaft 102 via a body 112 of the stirring element 106. While the head 110 and the body 112 of the stirring element 106 may be integrally formed by a single piece, according to an embodiment, the head 110 is provided as a separate element which is attached to the body 112 of the stirring element, the body 112 being attached to the shaft 102, as shown in FIG. 1.

In accordance with an embodiment, the recess 108 comprises a surface portion 114 and an edge 116 which defines an opening of the recess. The opening of the recess provides access to the surface portion 114.

FIG. 2 shows a side view of the stirring element 106 shown in FIG. 1 when viewed from line II-II in FIG. 1.

In accordance with an embodiment, the recess 108 is spaced from the shaft 102 by a distance which is about the length of the body 112 of the stirring element 106. When the shaft 102 is rotated in rotating direction 118, the corresponding rotation of the stirring element 106 defines a moving direction 120 of the recess 108 in which the edge 116 forms a leading edge of the recess 108. In other words, the moving direction 120 is always tangential to the moving path of the recess 108 about the axis of rotation 104 during a rotation of the shaft 102. Hence, the moving direction 120 is pointing in circumferential direction but relates to the moving reference system of the recess 108, while the circumferential direction is usually defined with regard to a fixed (not rotating) reference system in the three-dimensional space.

In accordance with an embodiment, the surface portion 114 defines a depth 122 of the recess 108 with regard to the edge 116. Further in accordance with an embodiment, in a radially inward direction 124 the depth 122 of the recess 108 is decreasing, as shown in FIG. 2.

According to an embodiment, the stirring element 106 comprises a further recess 126 pointing in the direction opposite to the recess 108. According to an embodiment, the recess 108 and the further recess 126 are configured symmetrically with regard to a plane of symmetry 128. According to an embodiment, the plane of symmetry 128 extends in radial direction 124.

FIG. 3 shows the stirring element 106 of FIG. 1 in greater detail.

In particular, FIG. 3 shows the head 110 of the stirring element 106 with the recess 108 and the further recess 126. As mentioned with regard to FIG. 2, the recess 108 comprises the surface portion 114 which defines a depth 122 of the recess 108 with regard to the edge 116 which forms an opening of the recess 108.

In accordance with an embodiment, the surface portion 114 comprises the radially inner part 129 and radially outer part 130, wherein the radially inner part 129 is located between the axis of rotation (not shown in FIG. 3) and the radially outer part 130. In other words, the radial distance of the radially outer part 130 from the axis of rotation is larger than the radial distance of the radially inner part 129 from the axis of rotation.

In accordance with a further embodiment, the edge 116 has a radially inner edge portion 144 and a radially outer edge portion 146, wherein the radially inner edge portion 144 is located between the axis of rotation (not shown in FIG. 3) and the radially outer edge portion 146. In other words, the radial distance of the radially outer edge portion 146 and the axis of rotation is larger than the radial distance of the radially inner edge portion 144 and the axis of rotation.

In accordance with an embodiment of the herein disclosed subject matter, the depth 122 of the recess 108 which is defined by the surface portion 114 and the edge 116 decreases in the radially inward direction 124, as shown in FIG. 3.

According to an embodiment, the depth of the recess is determined (measured) in moving direction. The decreasing depth in the radially inward direction 124 means that in the moving direction 120 the distance 132 between the radially outer part 130 and the edge 116 is larger than the distance 134 between the radially inner part 129 and the edge 116 (also measured in the moving direction).

The decreasing depth is, in an embodiment, achieved by the surface portion 114 being inclined by an angle 136 with regard to a plane 138 which is perpendicular to the moving direction 120. For example, in accordance with a more general embodiment, the surface portion 114 is configured such that the in a movement of the recess 108 in the moving direction 120 the radially inner part 129 is a leading part and the radially outer part 130 is trailing the radially inner part 129, as shown in FIG. 3.

Alternatively or additionally, the decreasing in depth is, in an embodiment, achieved by the edge 116 being inclined by an angle 140 with regard to the plane 142 which is perpendicular to the moving direction 120. For example, in accordance with a more general embodiment, the edge 116 is configured such that in a movement of the recess 108 in the moving direction 120 the radially outer edge portion 146 is a leading portion and the radially inner edge portion 144 is trailing the radially outer edge portion 146, as shown in FIG. 3.

It should be noted that the inclination of the surface portion 114 does not necessarily imply that the surface portion 114 is a flat surface. As described above, according to an embodiment the surface portion 114 may be curved. The same holds for the edge 116 which is not necessarily a straight edge but which might rather be curved in a respective embodiment. However, even the curved surface portion 114 or the curved edge 116 allow to determine a slope of the surface portion/edge, which slope provides a well defined inclination angle of the respective point on the surface portion 114 or the respective point on the edge 116.

In accordance with an embodiment, the recess 108 comprises a radially outer wall 150, a radially inner wall 152 and two sidewalls 154, one of which is shown in FIG. 3. In accordance with an embodiment, the surface portion 114 forms bottom of the recess, as shown in FIG. 3.

FIG. 4 shows the stirring element 106 of FIG. 3 when viewed from line IV-IV in FIG. 3.

FIG. 4 shows the radially outer wall 150, the radially inner wall 152 and the side walls 154. In accordance with an embodiment, the four walls 150, 152, 154 define the bottom of the recess 108 which is formed by the surface portion 114, in accordance with an embodiment. Further, the four walls 150, 152, 154 extend in the moving direction 120 (shown in FIG. 4) and are hence visible only with their cross-section. In accordance with an embodiment, the opening of the recess 108 has a tetragonal shape, e.g. rectangular shape as shown in FIG. 4.

In accordance with an embodiment, the body 112 of the stirring element 106 is formed by a metal beam which has an H-section, as can be taken from FIG. 3 and FIG. 4.

According to other embodiments, the body 112 of the stirring element is one of an I-section beam, a rectangular tube, a tube with circular or elliptical cross section, etc. Generally, any open or closed profile, e.g. an open or closed steel profile, may be suitable for the body 112.

FIG. 5 shows in cross-sectional view part of a further stirring element 206 in accordance with embodiments of the herein disclosed subject matter.

In accordance with an embodiment, the surface portion 114 extends in radial direction over less than 100%, e.g. over about 70%, of the radial extend 156 of the recess 108. In accordance with an embodiment, the recess 108 comprises a further surface portion 158, wherein the surface portion 114 is located between the further surface portion 158 and the axis of rotation (not shown in FIG. 5. In accordance with an embodiment, the further surface portion 158 defines a depth 160 of the recess 108.

In accordance with an embodiment, the further surface portion 158 comprises a first part 162 and a second part 164, wherein the second part 164 of the further surface portion 150 is located between the first part 162 and the radially outer part 130 of the surface portion 114. In other words, the radial distance between the first part 162 and the axis of rotation is larger than the radial distance between the second part 164 and the axis of rotation (not shown in FIG. 5).

In accordance with an embodiment, the depth 160 defined by the further surface portion 158 increases in the radially inward direction 124.

The increasing depth is, in an embodiment, achieved by the further surface portion 158 being inclined by an angle with regard to a plane which is perpendicular to the moving direction 120. For example, in accordance with a more general embodiment, the further surface portion 158 is configured such that the in a movement of the recess 108 in the moving direction 120 the first part 162 is a leading part and the second part 164 is trailing the first part 162, as shown in FIG. 3.

In accordance with an embodiment, the surface portion 114 and the further surface portion 158 abut in a kink 166.

In accordance with an embodiment, the surface portion 114 and the further surface portion 158 are both formed by flat surfaces which are provided by plate like metal elements welded together at the kink 166. Accordingly, the surface portion 114 extends straight in a direction 168 from its radially inner part 129 to its radially outer part 130. In this regard, should be understood that the term "plate like metal element" does not exclude such elements with chamfered edges.

In accordance with an embodiment, the edge 116 of the recess 108 comprises a radially innermost edge portion 170, wherein the radially inner part 129 of the surface portion 114 is located in the vicinity of the radially innermost edge portion 170. In accordance with an embodiment, the vicinity of any point on the radially innermost edge portion 170 is defined by a distance to this point which is less than 20% of the maximum depth of the recess in the moving direction, which according to an embodiment is the depth 172 of the recess 108 with regard to the edge 116 in the moving direction 120 at the position of the kink 166.

In accordance with an embodiment, the stirring element 206 comprises a radially inner wall 152 which extends in the moving direction 120, wherein the radially inner wall 152 of the recess 108 forms the radially innermost edge portion 170 of the edge 116 of the recess 108, as shown in FIG. 5.

In accordance with an embodiment, the surface portion 114 is abutting the radially inner wall 152 spaced by distance 174 from the radially inner edge portion 170.

FIG. 6 shows in cross-sectional view part of a further stirring element 306 in accordance with embodiments of the herein disclosed subject matter.

In accordance with an embodiment of, the recess 108 of the stirring element 306 comprises a surface portion 114 and the further surface portion in accordance with embodiments of the herein disclosed subject matter.

Further, in accordance with an embodiment the recess further comprises an intermediate surface portion 176 located between the surface portion 114 and the further surface portion 158, wherein the intermediate surface portion 176 connects the surface portion 114 and the further surface portion 158 to continuous surface of the recess 108. In accordance with an embodiment, the surface portion 114, the further surface portion 158 and the intermediate surface portion 176 form at least part of a bottom of the recess 108 or the entire bottom of the recess 108, as shown in FIG. 6.

In accordance with an embodiment, the surface portion 114 is curved in a direction 168 from its radially inner part 129 to its radially outer part 130, as shown in FIG. 6. In accordance with a further embodiment, the surface portion 114 extends straight in a first direction, wherein the first direction is parallel to the axis of rotation (not shown in FIG. 6, however the axis of rotation and hence in this embodiment the first direction extends perpendicular to the drawing plane of FIG. 6, as indicated in FIG. 6 at 177).

In accordance with an embodiment, the bottom 114, 158, 176 of the recess 108 is concave in radial direction so as to generate a flow 178 of fermentation material within the recess 108 in radial direction upon movement of the stirring element 306 through the fermentation material in the moving direction 120.

It should be noted that any entity disclosed herein (e.g. parts, portions, surfaces, components, units, structures and devices) is not limited to a dedicated entity as described in some embodiments. Rather, the herein disclosed subject matter may be implemented in various ways and with various granularity while still providing the specified functionality. Further, it should be noted that according to embodiments a separate entity (e.g. part, portion, surface, component, unit, structure or device) may be provided for each of the functions disclosed herein. According to other embodiments, an entity (e.g. part, portion, surface, component, unit, structure or device) is configured for providing two or more functions as disclosed herein. According to still other embodiments, two or more entities (e.g. part, portion, surface, component, unit, structure or device) are configured for providing together a function as disclosed herein.

It should be noted that the term "comprising" does not exclude other elements or steps and the "a" or "an" does not exclude a plurality. Also elements described in association with different embodiments may be combined. It should also be noted that reference signs in the claims should not be construed as limiting the scope of the claims.

Further, it should be noted that while the exemplary stirring devices in the drawings include a particular combination of several embodiments of the herein disclosed subject matter, any other combination of embodiment is also possible and is considered to be disclosed with this application.

In order to recapitulate some of the above described embodiments of the present invention one can state:

In accordance with embodiments of the herein disclosed subject matter it is described a stirring device 100 comprising a shaft rotatable about an axis of rotation; a stirring element 106 attached to the shaft, the stirring element 106 having a recess 108; the recess 108 having a surface portion 114 and an edge 116, the edge 116 defining an opening which provides access to the surface portion 114; the recess 108 being spaced from the shaft, wherein a rotation of the shaft defines a moving direction 120 of the recess 108 in which the edge 116 forms a leading edge of the recess 108; the surface portion 114 defining a depth 122 of the recess 108 with regard to the edge 116; and wherein in a direction 124 radially inwardly the depth 122 of the recess 108 is decreasing. In accordance with embodiments, the decreasing depth 122 may be realized by a suitable inclination 136 of the surface portion 114 of the recess 116 and/or by a suitable inclination 140 of the edge 116 of the recess 108.

LIST OF REFERENCE SIGNS 100 stirring device
102 shaft
104 axis of rotation
106, 206, 306 stirring element
108 recess
110 head
112 body
114 surface portion
116 edge
118 rotating (circumferential) direction
120 moving direction of 108
122 depth of 108 defined by 114
124 radially inward direction
126 further recess
128 plane of symmetry
129 radially inner part
130 radially outer part
132 distance between 130 and 116 in moving direction
134 distance between 129 and 116 in moving direction
136 angle of 114 with regard to 138
138 plane perpendicular to the moving direction
140 angle of 116 with regard to 142
142 plane perpendicular to the moving direction
144 radially inner edge portion
146 radially outer edge portion
150 radially outer wall
152 radially inner wall
154 sidewall
156 radial extent of 108
158 further surface portion
160 depth of 108 defined by 158
162 first part of 158
164 second part of 158
166 kink between 114 and 158
168 first direction of straight extension of 114
170 radially innermost edge portion
172 depth of 108 in the moving direction at 166
174 distance between 162 and 170
176 intermediate surface portion
178 movement of fermentation material within 108

The invention claimed is:

1. A stirring device configured for a biogas plug-flow fermenter for stirring a fermentation material comprising:
a shaft rotatable about an axis of rotation;
a stirring element attached to the shaft, the stirring element having a recess;
the recess having a surface portion and an edge, the edge defining an opening which provides access to the surface portion;
the recess being spaced from the shaft, wherein a rotation of the shaft defines a moving direction of the recess in which the edge forms a leading edge of the recess, the moving direction being always tangential to a moving path of the recess about the axis of rotation during a rotation of the shaft;

the surface portion defining a depth of the recess with regard to the edge;

wherein in a direction radially inwardly the depth of the recess is decreasing;

the surface portion extending straight in a first direction and being inclined with regard to a plane which is perpendicular to the moving direction;

wherein the first direction is parallel to the axis of rotation;

wherein the surface portion extends straight in a direction from its radially inner part to its radially outer part;

wherein the stirring element comprises a further recess pointing in the direction opposite to the recess; and wherein the recess and the further recess are configured symmetrically with regard to a plane of symmetry.

2. The stirring device according to claim 1, wherein the radially inner part is located between the axis of rotation and the radially outer part; and the surface portion being configured such that in a movement of the recess in the moving direction the radially inner part is a leading part and the radially outer part is trailing the radially inner part.

3. The stirring device according to claim 1, wherein the edge has a radially inner edge portion and a radially outer edge portion, wherein the radially inner edge portion is located between the axis of rotation and the radially outer edge portion; and the edge is configured such that in a movement of the recess in the moving direction the radially outer edge portion is a leading portion and the radially inner edge portion is trailing the radially outer edge portion.

4. The stirring device according to claim 1, wherein the recess comprises a further surface portion, wherein the surface portion is located between the further surface portion and the axis of rotation; and the further surface portion defines a depth of the recess with regard to the edge.

5. The stirring device according to claim 4, wherein the further surface portion has a first part and a second part, wherein the second part of the further surface portion is located between the first part of the further surface portion and the radially outer part of the surface portion; and the further surface portion being configured such that in a movement of the recess in the moving direction its first part is a leading part and its second part is trailing the first part.

6. The stirring device according to claim 4, wherein the recess further comprises an intermediate surface portion located between the surface portion and the further surface portion, the intermediate surface portion connecting the surface portion and the further surface portion to a continuous surface of the recess.

7. The stirring device according to claim 4, wherein the surface portion and the further surface portion are abutting in a kink.

8. The stirring device according to claim 1, wherein the surface portion extends in radial direction over at least 10% of a radial extent of the recess.

9. The stirring device according to claim 2, wherein the edge of the recess comprises an radially innermost edge portion, wherein the radially inner part of surface portion is located in the vicinity of the radially innermost edge portion of the edge, and wherein in the vicinity of any point on the radially innermost edge portion is defined by a distance to this point which is less than 50% of the maximum depth of a recess in the moving direction.

10. The stirring device according to claim 9, wherein the recess further comprises a radially inner wall which extends in the moving direction;

the radially inner wall of the recess forms the radially innermost edge portion of the edge of the recess; and the surface portion abutting the radially inner wall s spaced from the radially inner edge portion.

11. The stirring device according to claim 1, wherein the opening of the recess has a generally tetragonal shape.

12. The stirring device according to claim 1, wherein the plane of symmetry extends in radial direction.

13. The stirring device according to claim 2, wherein the recess comprises a further surface portion;

the surface portion is located between the further surface portion and the axis of rotation;

the further surface portion defines a depth of the recess; and the depth defined by the further surface portion increases in a radially inward direction.

14. The stirring device according to claim 1, wherein the surface portion extends in a radial direction over less than 100% of a radial extent of the recess.

* * * * *